United States Patent
East et al.

(10) Patent No.: US 10,364,251 B2
(45) Date of Patent: Jul. 30, 2019

(54) POLYESTERS FROM ASSYMETRICAL MONOMERS BASED UPON BISANHYDROHEXITOLS

(71) Applicant: New Jersey Institute of Technology, Newark, NJ (US)

(72) Inventors: Anthony East, Madison, NJ (US); Willis Hammond, Chatham, NJ (US); Michael Jaffe, Maplewood, NJ (US); Xianhong Feng, Kearny, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 179 days.

(21) Appl. No.: 15/423,361

(22) Filed: Feb. 2, 2017

(65) Prior Publication Data
US 2017/0210750 A1  Jul. 27, 2017

Related U.S. Application Data

(62) Division of application No. 13/050,304, filed on Mar. 17, 2011, now Pat. No. 9,580,544.

(60) Provisional application No. 61/315,227, filed on Mar. 18, 2010.

(51) Int. Cl.
| | | |
|---|---|---|
| *C07D 493/04* | (2006.01) | |
| *C07D 519/00* | (2006.01) | |
| *C08G 63/66* | (2006.01) | |
| *C08G 63/664* | (2006.01) | |
| *C08G 63/672* | (2006.01) | |

(52) U.S. Cl.
CPC ......... *C07D 493/04* (2013.01); *C07D 519/00* (2013.01); *C08G 63/66* (2013.01); *C08G 63/664* (2013.01); *C08G 63/672* (2013.01); *Y02P 20/55* (2015.11)

(58) Field of Classification Search
CPC .... C07D 493/04; C07D 519/00; C08G 63/66; C08G 63/664; C08G 63/672; Y02P 20/55
See application file for complete search history.

(56) References Cited

U.S. PATENT DOCUMENTS

| 4,297,286 A | 10/1981 | Sandrock et al. |
| 4,435,586 A | 3/1984 | Kruse et al. |
| 4,769,379 A | 9/1988 | Leitold et al. |
| 6,169,124 B1 | 1/2001 | Horn et al. |
| 6,737,481 B1 * | 5/2004 | Kurian ............... C08G 63/672 524/483 |
| 2003/0232959 A1 | 12/2003 | Adelman et al. |
| 2007/0267599 A1 | 11/2007 | Goldfinger et al. |
| 2007/0282042 A1 | 12/2007 | East |
| 2008/0021209 A1 | 1/2008 | East et al. |
| 2008/0212009 A1 | 9/2008 | Nakano |

FOREIGN PATENT DOCUMENTS

| CN | 1675265 A | 9/2005 |
| CN | 101648958 A | 2/2010 |
| DE | 3123719 | 1/1983 |
| JP | 200364170 | 3/2003 |
| JP | 2005530000 | 10/2005 |
| JP | 2010503736 | 2/2010 |
| KR | 20050089743 | 9/2005 |
| WO | 0100237 | 1/2001 |
| WO | 2004060939 A1 | 7/2004 |
| WO | 2009146202 | 12/2009 |

OTHER PUBLICATIONS

Trahanovsky et al."Isosorbide Esters.." Fuel Chemistry Division Preprints 2002, 47(1), 368.*
Storbeck et al."Synthesis and properties of high-molecular-weight polyesters based on 1,4: 3,6-dianhydrohexitols and terephthalic acid", Makromol. Chem. 194, 53-64 (1993).*
Thiem et al. "Synthesis of Polyterephthalates Derived from Dianhydrohexitols", Polymer Butletin 11, 365-369 (1984).*
Chatti et al., "Synthesis and properties of new poly(ether-ester)s containing aliphatic diol based on isosorbide. Effects of the microwave-assisted polycondensation", "European Polymer Journal", Oct. 1, 2005, pp. 410-424, vol. 42, No. 2.
Qiyi Xin et al., "Basic Organic Chemistry", Jun. 30, 1994, p. 956 Publisher: High Education Press.

* cited by examiner

*Primary Examiner* — Ling Siu Choi
*Assistant Examiner* — Gennadiy Mesh
(74) *Attorney, Agent, or Firm* — Davis, Brown, Koehn, Shors & Roberts, P.C.; Matthew W. Coryell (57) ABSTRACT

An AB monomer, useful for the production of condensation polymers, wherein the AB monomer has the structure: A—X—C—Y—B; wherein A is a carboxylic acid or ester or reactive carbonyl derivative, Y is a bisanhydrohexitol unit derived from isosorbide, isoidide or isomannide; X is selected from the group consisting of aromatic rings, substituted or unsubstituted heterocycles, and saturated or unsaturated aliphatic chains; and B is OH and C is an ester carbonyl link with the carbon attached to X and the oxygen attached to Y, and wherein the AB monomer is at least about 98% pure endo-substituted bisanhydrohexitol derivative or an at least about 98% pure exo-substituted bisanhydrohexitol derivative.

4 Claims, 10 Drawing Sheets

POLYESTERS FROM ASSYMETRICAL MONOMERS BASED UPON BISANHYDROHEXITOLS

CROSS-REFERENCE TO RELATED APPLICATION(S)

This application is a divisional application of U.S. patent application Ser. No. 13/050,304, filed Mar. 17, 2011, which claims priority to claims priority to U.S. Patent Application Ser. No. 61/315,227, filed Mar. 18, 2010, each of which is incorporated herein by this reference in its entirety.

BACKGROUND OF THE INVENTION

The present invention relates generally to asymmetrically substituted compounds and, more specifically, to asymmetrically substituted derivatives of bisanhydrohexitols, including isosorbide and isoidide, that may be used as monomers in polymerization reactions.

Isosorbide is a stable, rigid, dihydroxyether derived from glucose by reduction to sorbitol and acid-catalyzed cyclo-dehydration. It belongs to a class of compounds called bisanhydro-hexitols, other members being isomannide (from mannose) and isoidide (from idose). Such materials are water soluble and harmless and find widespread use in pharmaceuticals and food chemistry. By far the most widely available is isosorbide, which can be obtained from biomass sources via enzyme hydrolysis to make simple hexose sugars and subsequent hydrogenation to make sugar alcohols. Isosorbide is increasingly becoming used as an intermediate and raw material for polymers, additives and stabilizers.

One of the great advantages of isosorbide, unlike its isomers, is that it has two hydroxyl groups with different topographies and chemical reactivity. One —OH is exo and one is endo and as a result they can be selectively esterified and etherified by use of specific chemical reactions under the correct conditions. This invention discloses a range of products and additives in which this idea is exploited to make useful, stereo-defined monomers and polymers based on isosorbide. Incorporation of isosorbide into PET has been shown to raise the Tg of the resulting co-polymer affording a copolymer that has potential as a hot fill bottle resin. However, simple incorporation of isosorbide into PET on a commercial scale has encountered several problems. The secondary hydroxyl groups of isosorbide make it less reactive than the primary hydroxyls of ethylene glycol. This fact coupled with the volatility of isosorbide make it difficult to get high incorporation into PEIT copolymers and leads to complications with the recycle of the ethylene glycol/isosorbide stream generated during polymerization. It is believed that the different reactivities of the two hydroxyl groups of isosorbide also complicate its polymerization chemistry.

SUMMARY OF THE INVENTION

The present invention consists of novel asymmetrically substituted compounds that are derivatives of bisanhydrohexitols. The compounds have applicability as asymmetric or so-called AB monomers in polymerization reactions.

The process for making the compounds of the present invention selectively reacts a bisanhydrohexitol either with a protective moiety to protect one of the —OH groups of the bisanhydrohexitol, or by application of selective reaction kinetics to make the desired compound. In the latter case, no de-protection step is needed. The substituted, protected bisanhydrohexitol is then reacted with a selected acid to attach it to the protected bisanhydrohexitol at the selected —OH group via an ester linkage. A protective moiety can be removed to provide the asymmetrically substituted bisanhydrohexitol. The acid is preferably selected from substituted and unsubstituted aromatic acid, aliphatic unsaturated and alicyclic acids, and their derivatives. The following examples are given below, but the invention is not limited to these compounds alone and other examples will be apparent to those skilled in the art.

Isosorbide terephthalate esters and an isoidide terephthalate ester have been synthesized from isosorbide in high purity and characterized, such as isosorbide 5-(4-carbomethoxybenzoate) (denominated herein as compound 1), isosorbide 2-(4-carbomethoxybenzoate) (denominated herein as compound 2), and isoidide 2-(4-carbomethoxybenzoate) (denominated herein as compound (3). In addition, homopolymers have been synthesized from these AB monomers by a novel method of self-polymerization, which homopolymers not only have regioselectivity but also represent a new class of polymers. It will at once be apparent to those skilled in the art that the two monomers 1 and 2 will give the SAME regioregular homopolymer. This appears to be true from their physical properties. The new homopolymers exhibit a definite melting point evidencing crystallinity. These monomers moreover can be introduced into condensation polymers, such as poly(ethylene terephthalate) (PET) to introduce improved properties into the condensation polymers.

An object of the present invention is to provide novel asymmetrically substituted bisanhydrohexitols.

Another object of the present invention is to provide novel AB monomers comprising asymmetrically substituted bisanhydrohexitols that can be polymerized through a novel self-polymerization reaction to provide novel homopolymers.

A further object of the present invention is the addition of the novel monomers and or homopolymers to condensation polymers to produce condensation copolymers having novel and improved characteristics notably a degree of regiospecific character.

Yet another object of the present invention is to introduce an bisanhydrohexitol moiety into a polyester with reduced loss of the bisanhydrohexitol during polymerization.

These and other objects of the present invention will be made apparent to those skilled in the art upon a review and understanding of this specification, including the figures, and the appended claims.

DETAILED DESCRIPTION OF PREFERRED EMBODIMENTS THE INVENTION

A. Preparation of AB Monomers

1. Preparation of Isosorbide 2-benzyloxy-5-(4-carbomethoxybenzoate) (6)

Into 500 ml 3-necked flask equipped with magnetic stirrer, pressure equalizing dropping funnel, and drying tube was charged 28.35 g (0.12 mole) isosorbide-2-benzyl ether (4), 100 ml methylene chloride and 30 ml (0.215 mole) dry triethylamine. 4-Carbomethoxy-benzoyl chloride (5) (0.15 mole) in 120 ml methylene chloride was added dropwise over 1 hour. The reaction was stirred overnight. The next morning the reaction mixture in methylene chloride was poured into a 1 liter separatory funnel and washed with 2×150 mls 15% v/v hydrochloric acid followed by washing with 100 ml saturated aqueous sodium bicarbonate and 100 ml brine. The product in methylene chloride was dried for 2 hrs over anhydrous sodium sulfate at 8° C., filtered and the methylene chloride removed on a Rotavap to give 57.1 g of reddish solid (0.14 moles crude). The product was dissolved in 600 ml hot methanol and allowed to crystallize in the refrigerator overnight. The next morning the methanol solution was filtered to yield 41 g of white solid (87% yield after vacuum drying) mp 90-91° C.

2. Preparation of Isosorbide 5-(4-carbomethoxybenzoate) (1)

Isosorbide 2-benzyloxy-5-(4-carbomethoxybenzoate) (6) (35.0 g, 0.088 mole) was added to 0.61 g of pre-reduced 10% Pd/C suspended in 200 ml of methanol and reduced with hydrogen at an initial pressure of 85 psi. When the theoretical amount of hydrogen had been absorbed, the system was vented. An additional 200 mls methanol was added to the reduction product, warmed to dissolve the product and filtered through Whatman #1 filter paper to remove the catalyst. The methanol solution was concentrated to ca. 250 mls with heating. On cooling, 22.6 g (0.0733 mole, 83.4% yield) of 1 as a white solid, mp 154-155° C. was isolated. The reactions are illustrated in Scheme 1.

Scheme 1: Isosorbide 5-(4-carbomethoxybenzoate), Isosorbide 5-TA AB monomer 1

3. Preparation of Isosorbide 5-benzyloxy-2-(4-carbomethoxybenzoate) (8)

Into a 500 ml 3-necked flask equipped with magnetic stirrer, pressure equalizing dropping funnel, and drying tube was charged 28.35 g (0.12 mole) isosorbide-5-benzyl ether (7), 100 ml methylene chloride and 30 ml (0.215 mole) dry triethylamine. 4-Carbomethoxy-benzoyl chloride (5) (0.15 mole) in 120 ml methylene chloride was added dropwise over 1 hour. The reaction was stirred overnight. The next morning the reaction mixture in methylene chloride was poured into a 1 L separatory funnel and washed with 2×150 mls 15 v/v % hydrochloric acid followed by washing with 100 ml saturated aqueous sodium bicarbonate and 100 ml brine. The product in methylene chloride was dried for 2 hrs over anhydrous sodium sulfate at 8° C., filtered and the methylene chloride removed on a Rotavap to give 56.5 g. solid (0.14 moles crude). The product was dissolved in 700 ml hot methanol, treated with activated carbon, filtered, and allowed to crystallize in the refrigerator overnight. The next morning the methanol solution was filtered to yield 37.4 g of white solid (78% yield after vacuum drying) mp 100-101° C.

4. Preparation of Isosorbide 2-(4-carbomethoxybenzoate), Isosorbide 2-TA AB monomer (2)

0.60 g 10% Pd/C was suspended in 200 ml methanol and pre-reduced with hydrogen. The hydrogen was vented and 35.33 g (0.088 mole) of isosorbide-5-benzyloxy-2-(4-carbomethyoxybenzoate) (8) was added. After several purges with nitrogen and evacuation, the manifold was pressurized to 90 psi, the magnetic stirrer was turned on and the hydrogenation was allowed to continue overnight. The starting material was not very soluble in methanol so a water bath was placed around the hydrogenation vessel and heated to 41-43° C. with the hotplate of the stirrer set to low. The pressure dropped and remained steady at 39 psi. Total hydrogen uptake was 51 psi (theoretical, 46.5 psi). The hydrogen was vented and the methanol solution was filtered through a Whatman #1 fluted filter paper to remove the catalyst. The flask and catalyst were washed with an additional 200 ml of methanol. The combined methanol solutions were evaporated to dryness on a Rotavap to yield 23.14 g white solid which by NMR was >98% pure, mp 139-141° C. The reactions are illustrated in Scheme 2.

removed on the Rotavap to yield a brown oil. The oil was dissolved in 50 ml hot methanol and refrigerated to crystallize. The crystals were isolated by filtration and recrystallized again from hot methanol to yield 8.47 g (42% yield) of isoidide 2-(4-carbomethoxybenzoate)-5-benzyl ether, mp 59° C. The reactions are illustrated in Scheme 3.

Scheme 2: Isosorbide 2-(4-carbomethoxybenzoate), Isosorbide 2-TA AB monomer (2)

Scheme 3: Isoidide 2-(4-carbomethoxybenzoate), Isoidide 2-TA AB monomer

5. Preparation of Isoidide 2-(4-carbomethoxybenzoate), Isoidide 2-TA AB monomer (11)

In a 500 ml 3-necked flask equipped with a reflux condenser, nitrogen purge and magnetic stirrer was mixed 2-benzyloxy-isosorbide-5-tosylate (9) (19.58 g, 0.05 mole), potassium 4-carbomethoxybenzoate (10) (13.49 g, 0.061 mole) and 50 mls dry dimethylformamide. The reaction mixture was heated to 150° C. in as temperature controlled oil bath for 5 hours and slowed to cool overnight. The reaction mixture formed a semisolid mass on cooling. The reaction mixture was washed into a separatory funnel with 250 ml water and 150 ml methylene chloride. The methylene chloride layer was separated and the aqueous layer was washed with 2×150 mls methylene chloride. The combined methylene chloride extracts were washed with 200 mls saturated aqueous sodium bicarbonate and 100 mls brine before drying with anhydrous sodium sulfate. The sodium sulfate was removed by filtration and the methylene chloride B. Preparation of Polymers from the Monomers 1. Polymerization of Isosorbide 5-(4-Carboxymethoxybenzoate) (1)

The polymerization was run in the melt in a glass mini-polymerization reactor apparatus designed to take 10-20 grams of monomer. It was stirred with a sealed Herschberg nichrome wire stirrer and immersed in a tall oil-bath heated and controlled by a digital power unit. The polymerizer was connected directly to a high vacuum trap and a vacuum pump capable of achieving 0.01 mm Hg. All the melt polymerizations described below were run in very much the same way.

The cold apparatus was charged with 10.0 g of isosorbide 5-(4 carbomethoxybenzoate) (1) (mp 154-55° C.) and exhausted to 0.01 mm Hg to dry out the apparatus and monomer and remove all traces of moisture and other volatiles. Next the vacuum was released with dry nitrogen and the catalyst added, a solution of 5.0 µl of (liquid) titanium tetra-isopropoxide (TTiP) dissolved in 1.0 ml of dichloromethane added from a micro-syringe through a septum in the side arm. The polymerization vacuum was 0.05 mm Hg. The oil bath was raised to 160° C. for two hours and the melt agitated for one additional hour at 160° C. while it bubbled. After this, the bubbling died down and the melt was quite viscous. The batch was raised to 190° C. in increments of 20° C. per hour. The vacuum was maintained at 0.05 mm Hg. The bath was then raised to 265° C. over an additional hour and stirred at this temperature for one hour more. It grew very viscous and began to stick to the stirrer and also discolor. The vacuum was let down with dry nitrogen and the system cooled rapidly to room temperature. The isolated brown solid weighed 5.8 g.

Figure 1:
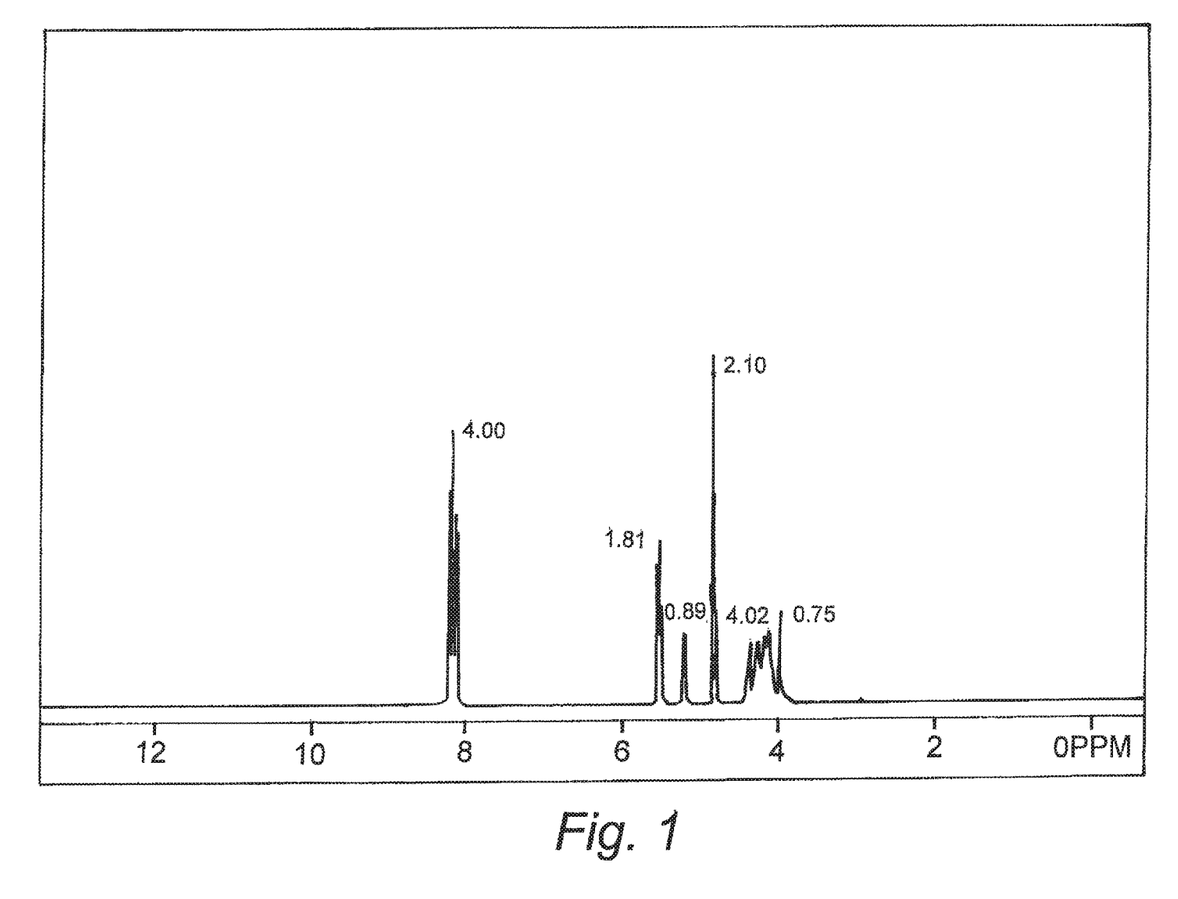
FIG. 1 is the 300 MHz 1H NMR spectrum (in TFA-d) of polymerized 1.
Figure 2:
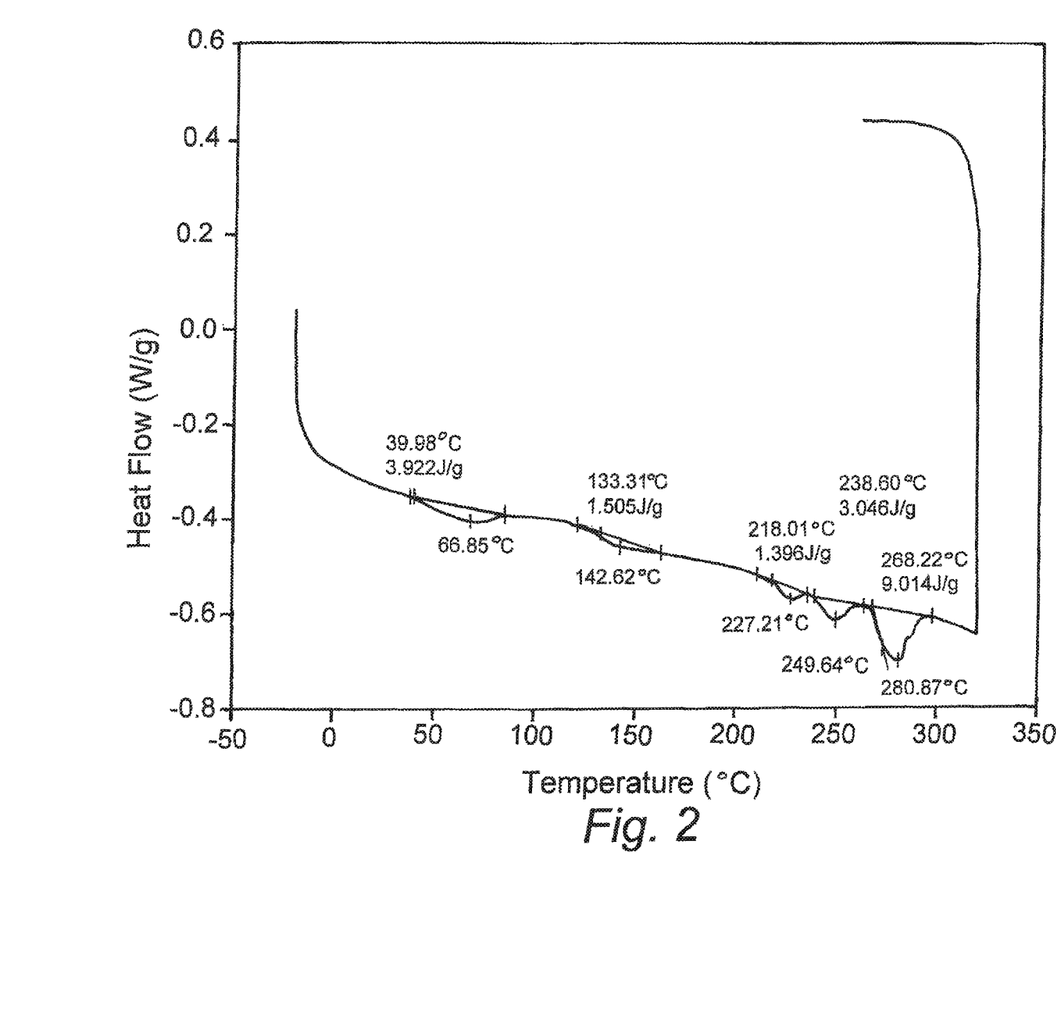
FIG. 2 is a chart of the DSC analysis of polymerized 1.

The solid was ground to a powder and a portion dissolved in TFA-d for NMR studies. The NMR spectrum (FIG. 1) was consistent with the desired structure with a low MW and a DP of about 4 (as judged by the end-groups). This corresponds to a Mn of ca 1200 g/mole. The DSC (FIG. 2) showed a complex pattern of Tm endotherms and no easily-recognizable Tg. However, after annealing under nitrogen at 240° C., (FIG. 3) a well-defined Tg at 145° C. was seen and a Tm around 240° C.

2. Polymerization of Isosorbide 2-(4-Carbomethoxybenzoate) (2) to polymer (12)

Figure 4:
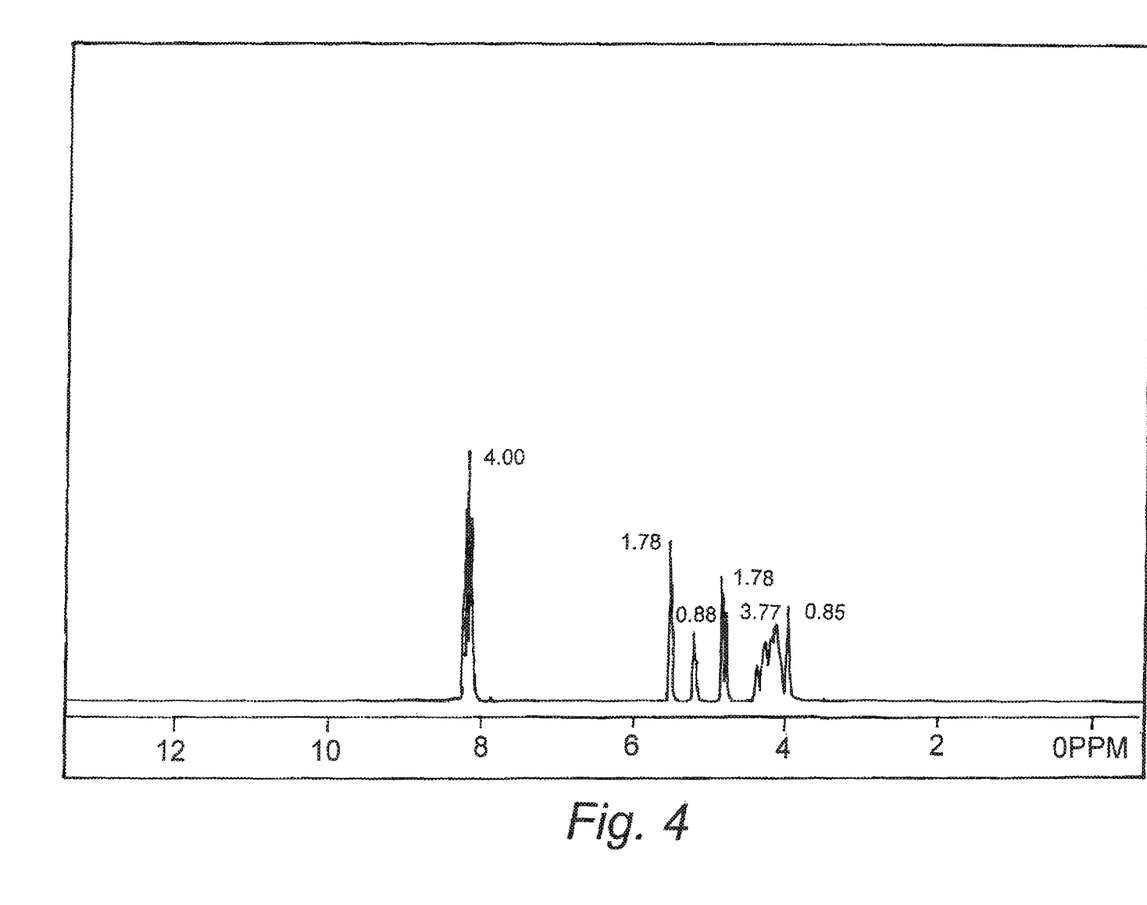
FIG. 4 is the 300 MHz 1H NMR spectrum (in TFA-d) of polymerized 2.
Figure 5:
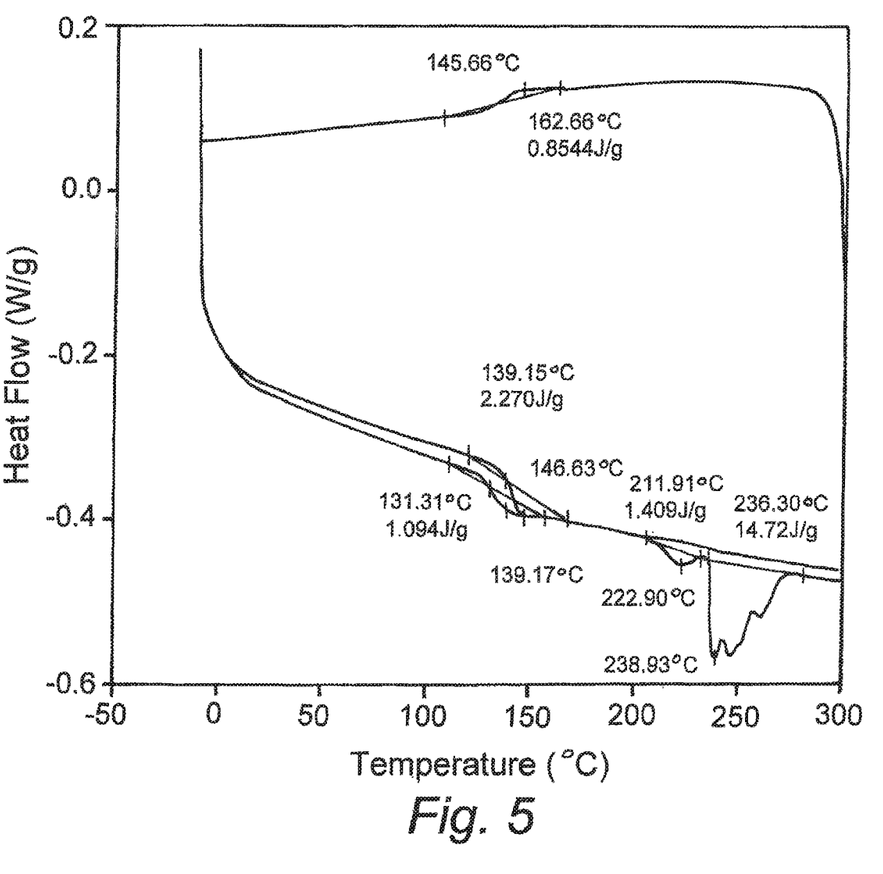
FIG. 5 is a chart of the DSC analysis of polymerized 2.

The polymerization followed the same route with an identical amount of TTiP catalyst and the same protocols for drying out the apparatus under vacuum. The melt polymerization was commenced by heating the batch up to 170° C. over two hours from ambient under a vacuum of 0.1 mm Hg. The melt was held for another thirty minutes at 170° C. until it ceased bubbling. Then the bath was raised to 280° C. in increments of 25° C. per hour, still under the same vacuum. The viscous melt was held at 280° C. for one hour then the vacuum let down with nitrogen and the system cooled to room temperature. The polymer melt had darkened noticeably at 280° C. When cool, the dark brown solid was isolated and weighed about 5 grams. It was ground up and a portion dissolved in TFA-d for the usual NMR spectrum. The NMR (FIG. 4) showed the expected structure with a DP of 4, corresponding to a Mn about 1200 g per mole. The DSC trace (FIG. 5) showed a Tg about 145° C., while the Tm at this stage was absent. Annealing at 240° C. for 8 hours under dry nitrogen raised the Tg slightly to 145-150° C. (FIG. 6) while the Tm endotherm became easily recognizable and corresponded to a Tm of about 240° C.

Results

The two AB monomers of interest have been synthesized as disclosed. It appears that, as expected, monomers (1) and (2) give the same homopolymer ((12) in scheme 5).

Using the Sn2 inversion chemistry we have also prepared an isoidide terephthalate ester (3). The Sn2 reaction gave the benzyl ether 45 in modest yield (42%). Addition of 18-crown-6 as a phase transfer catalyst gave a significant amount of dimethyl terephthalate apparently from disproportionation of 44 and a low yield of 45. The yield of 45 could be increased by adding 44 to the hot reaction mixture in small portions over an hour at 150° C. Hydrogenation of 45 gives the desired monomer 3.

Poly(isosorbide terephthalate) (13) has been synthesized by solution polymerization (Storbeck, R., Rehahn, M. and Ballauff, M., Synthesis and Properties of High-Molecular Weight Polyesters based on 1,4:3,6-Dianhydrohexitols and Terephthalic Acid, Makromol. Chem, 194, 53-64 (1993)). In this polymer the isosorbide units which have two possible orientations in the polymer chain are incorporated in ransom order as illustrated in Scheme 4.

Scheme 4: Synthesis of PEIT (13) with random orientation of Isosorbide

Figure 3:
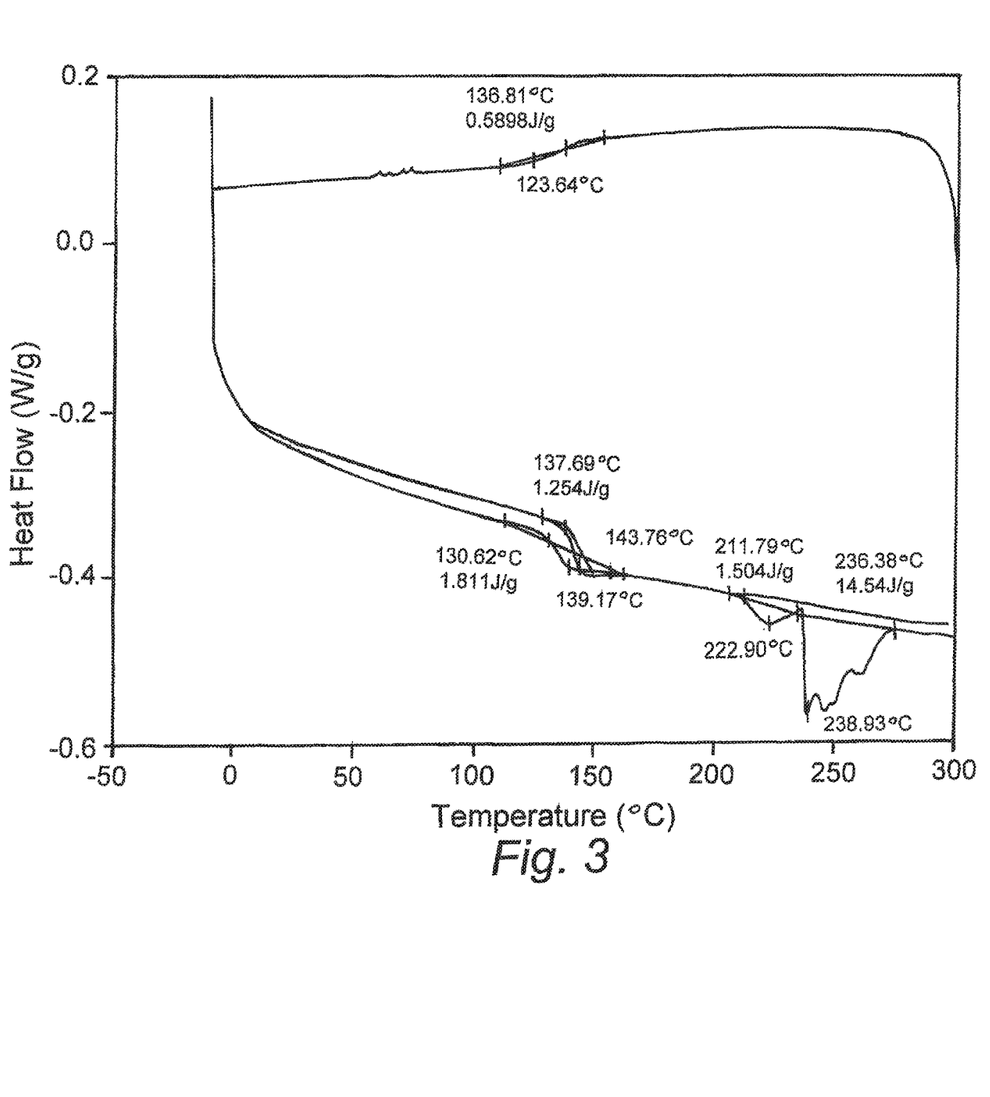
FIG. 3 is a chart of the DSC analysis of polymerized 1 after annealing.
Figure 6:
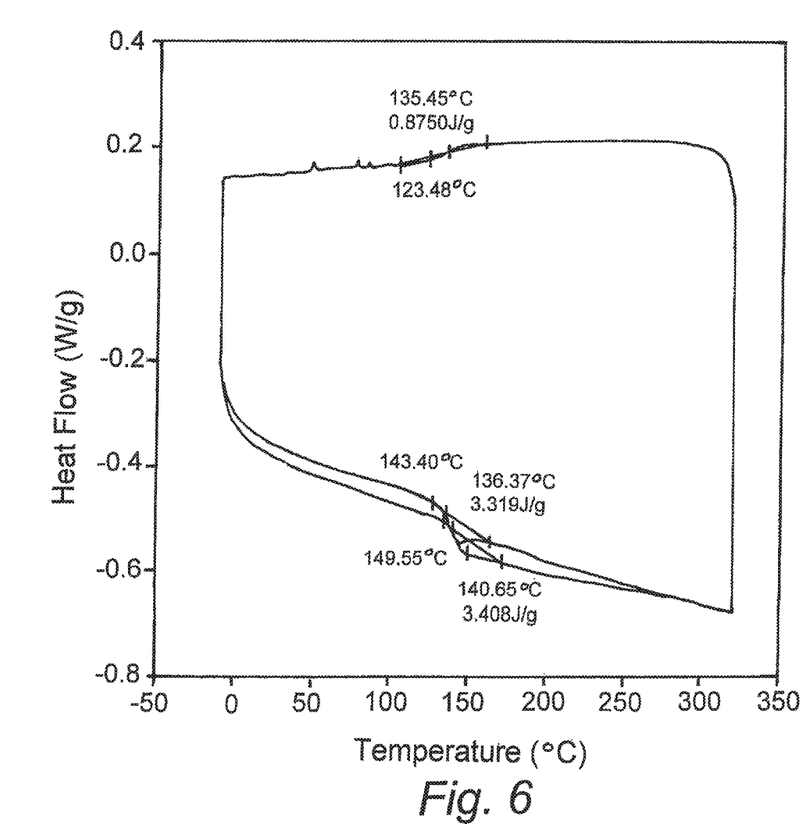
FIG. 6 is a chart of the DSC analysis of polymerized 2 after annealing.

Using the AB-monomers (1) and (2) should lead to a polymer with stereoregular ordering of the isosorbide as illustrated in Scheme 5. This polymer should have different properties than the polymer with random orientation mentioned above. While (1) and (2) give the same stereoregular polymer as illustrated in scheme 5, we expect that they will have different rates of polymerization because (1) has an exo hydroxyl group and (2) has an endo hydroxyl group. Polymers prepared from (1) and (2) have very similar 1H NMR spectra (FIGS. 1 and 4, respectively) and DSC thermograms (FIGS. 3 and 6, respectively.)

3. Incorporation of Isosorbide-5-(4-carbomethoxybenzoate) (1) into PET 17.35 g (0.09 mole) PET (identified as IMPET, Tg 2nd, Mp 81.5° C., FIG. 7) and 3.08 g (0.01 mole) of 1 were mixed in the microreactor. The reactor was purged with oxygen free nitrogen and heated to 270° C. in a fluidized bed heater. When the PET had melted the stirrer was turned on and the reactor was evacuated to <0.1 mm of Hg. After 30 minutes the temperature was raised in 5° C. increments every 15

Scheme 5: Synthesis of stereoregular PEIT (12) from AB monomers 1 or 2.

Figure 7:
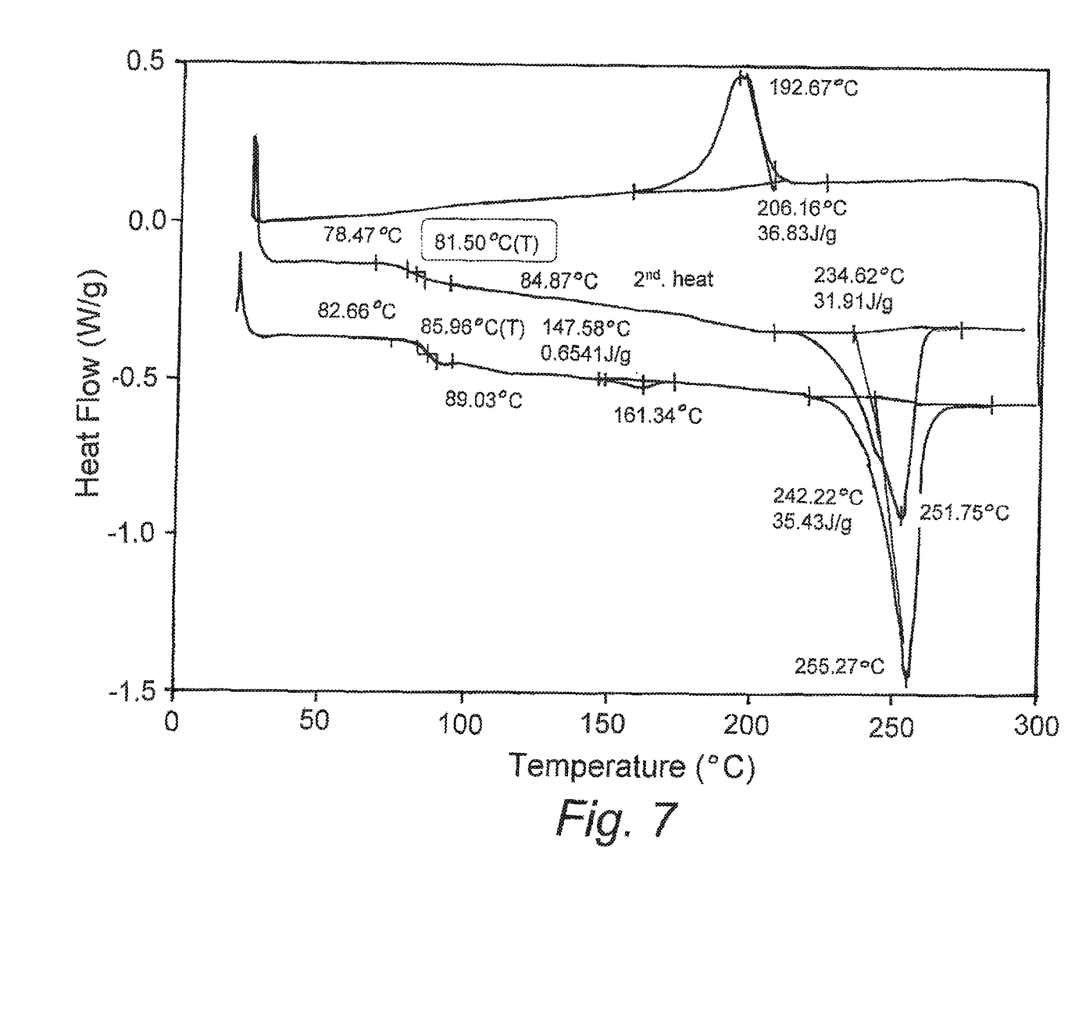
FIG. 7 is a chart of the DSC of PET (IMPET) used in copolymerization with 1.
Figure 8:
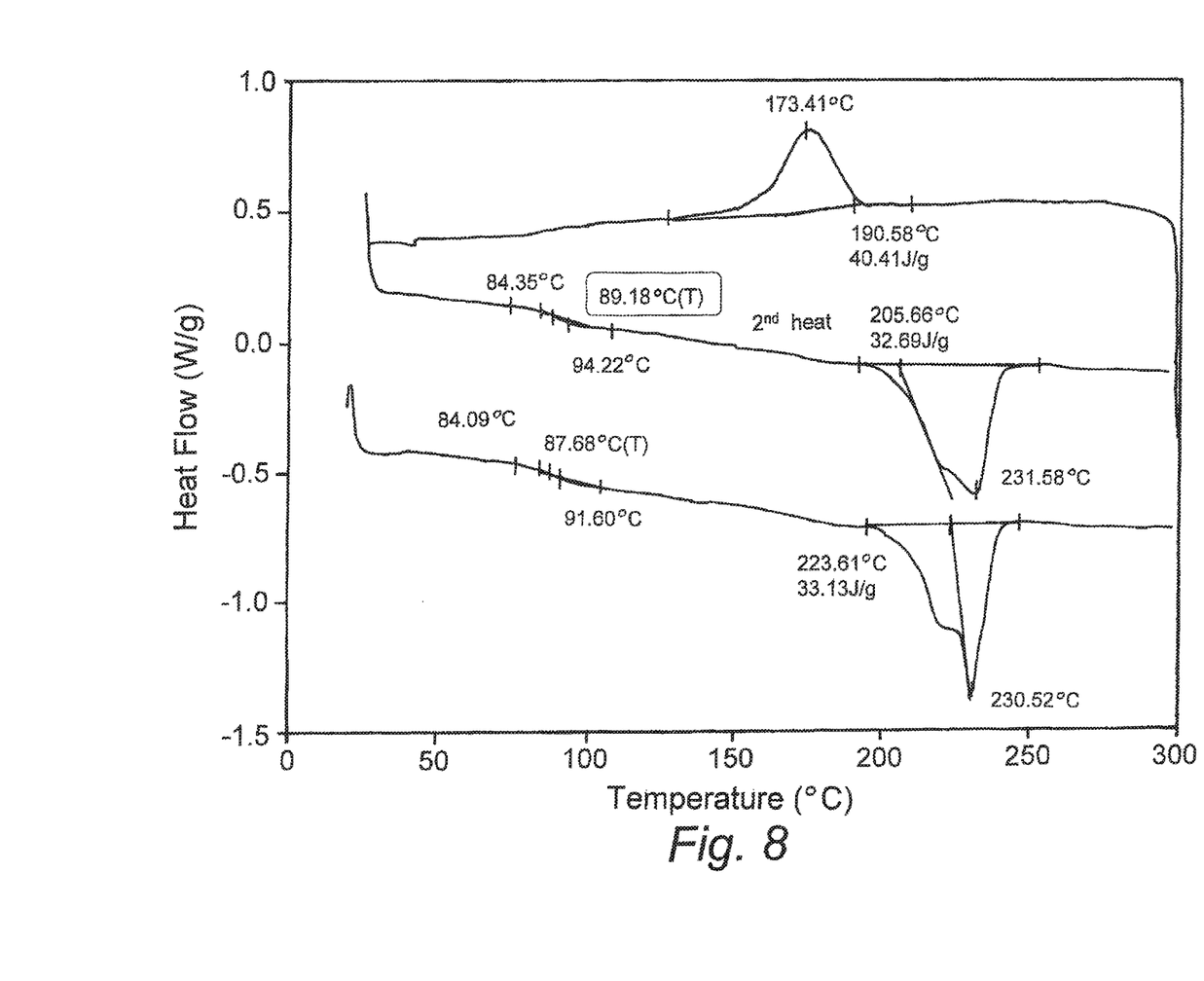
FIG. 8 is a chart of the DSC of PET (IMPET)+10% 1.
Figure 9:
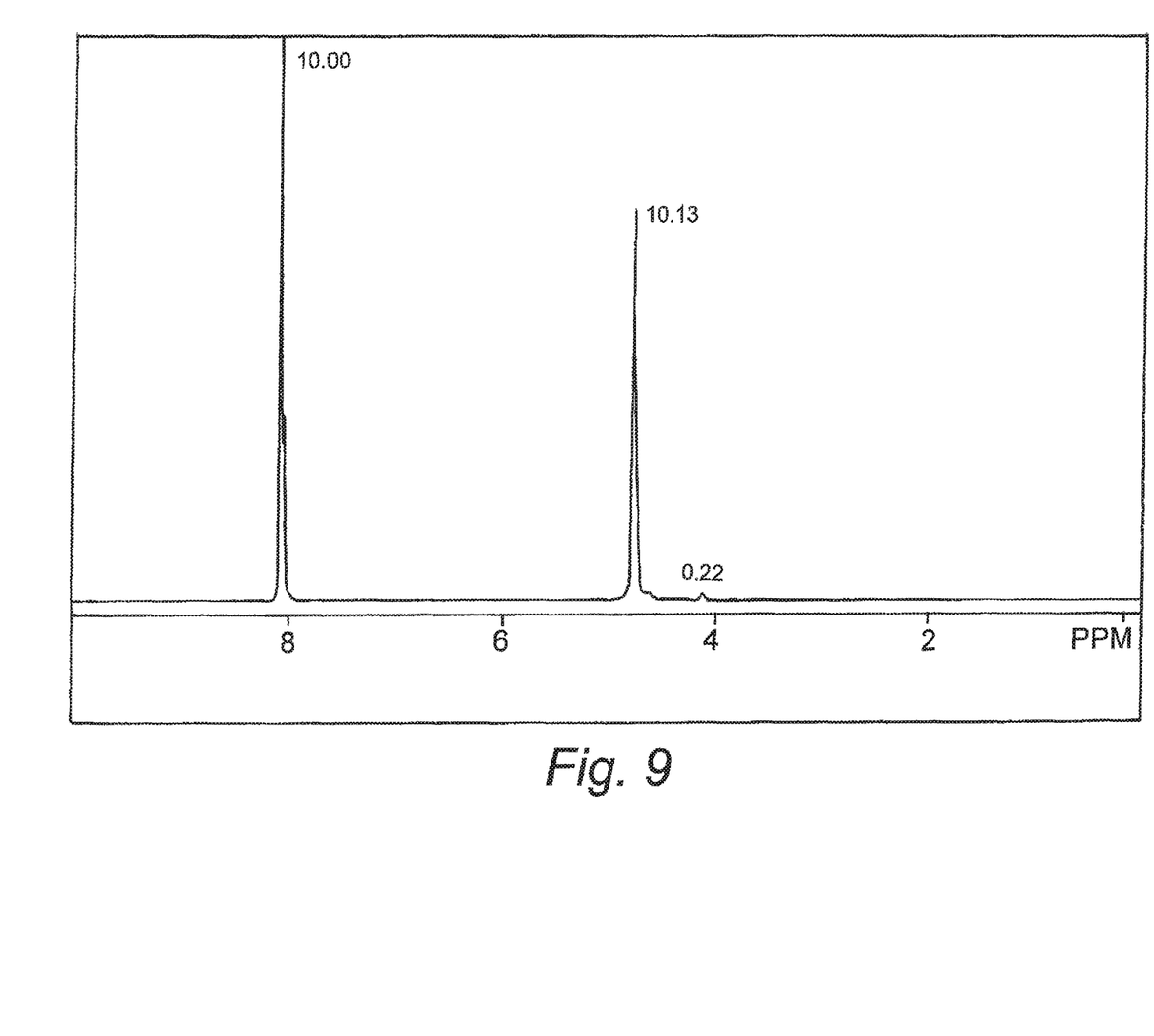
FIG. 9 is the 300 MHz 1H NMR spectrum) in TFA-d) of PET(IMPET) showing. 2% DEG.

We have surprisingly observed that polymer (12) shows a Tm on annealing in contrast to polymer (13) which is reported to be amorphous (Storbeck et al., supra). We have also observed that polymer (12), made from either monomer (1) or (2) are remarkably similar as shown in scheme 5.

minutes to a temperature of 290° C. where it was maintained for 4 hrs. The reactor was then removed from the fluidized bed heater, the stirrer was raised and the reactor was allowed to cool. FIG. 7 shows the DSC of the PET used in the copolymerization experiment. The starting PET has a Tg of 81.5° C. (2nd heat) and an MP of 255° C. The polymer resulting from copolymerization of PET with isosorbide 5-TA, 1, gave a Tg of 89.2° C. 2nd melt and a Mp of 232° C. (FIG. 8) for an increase in Tg of 7.7° C. 1H NMR analysis of the starting PET (FIG. 9, H2372) detected no copolymer with the exception of 2.2 mole % of DEG (diethylene glycol) which is formed from ethylene glycol during the manufacture of PET.

Figure 10:
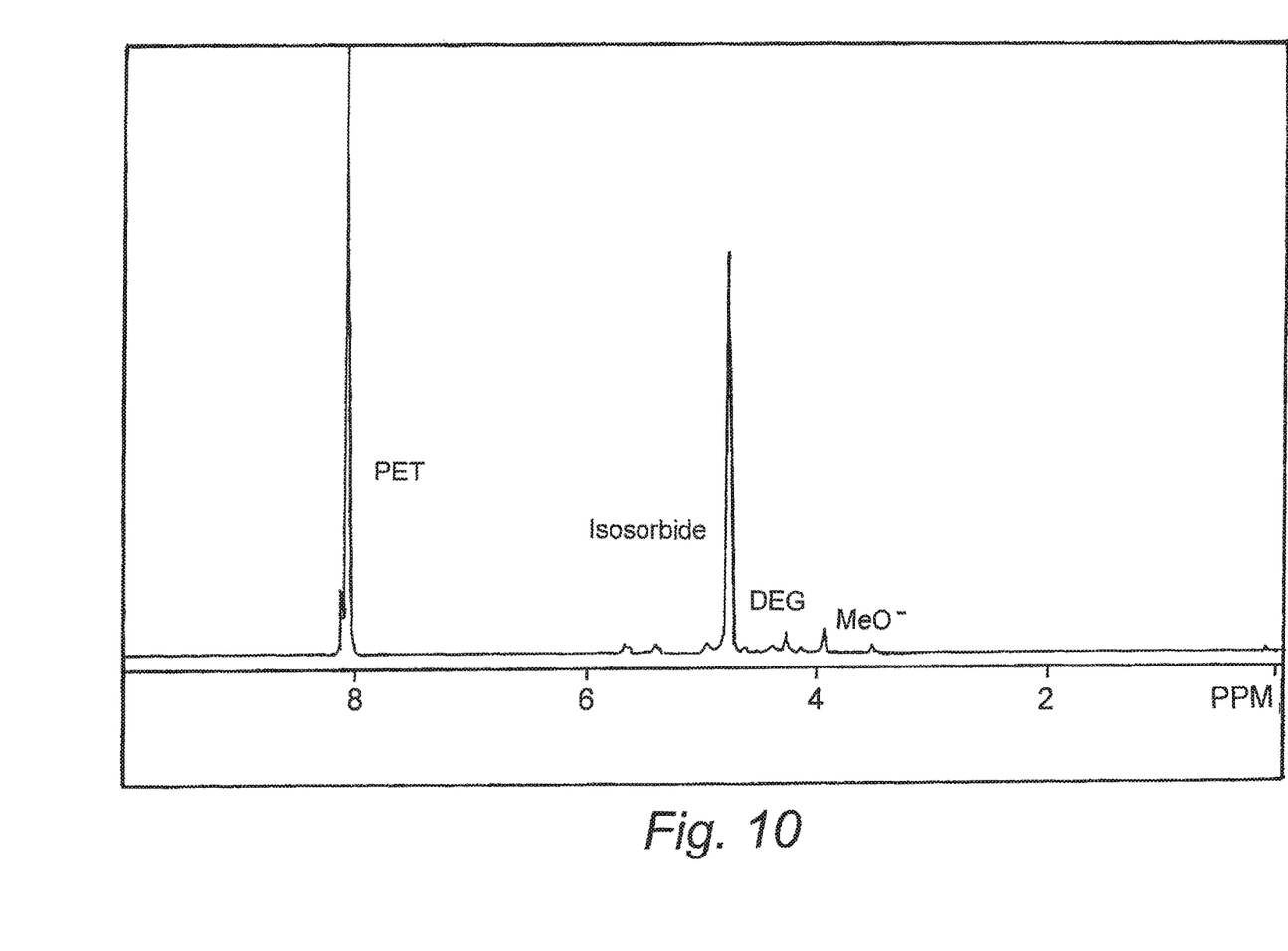
FIG. 10 is the 300 MHz 1H NMR spectrum (in TFA-d) of PET (IMPET) polymerized with 10% 1.

The 1H NMR spectrum (FIG. 10) of the PET-isosorbide-5-(4-carbomethoxybenzoate) (1) copolymer show the expected major peaks at 8.1 and 4.75 ppm for PET and peaks between 4 and 5.7 ppm expected for incorporation of isosorbide into the polymer. The chemical shift and integrated intensities of the isosorbide peaks compare very closely to the peaks seen in the isosorbide-5-(4-carbomethoxybenzoate) homopolymer (1). A peak at 3.93 ppm is assigned to the methoxy terephthalate end group of the copolymer. No evidence was found for the presence of an isosorbide end group as demonstrated by no measurable change in the NMR spectrum of the copolymer in TFA-d on addition of trifluoroacetic anhydride. The 2-hydroxy group of an isosorbide end group would have formed a trifluoroacetate ester and the methane proton would have shifted to ca. 5.6 ppm and been detected in the integrated spectrum. From the integrated intensities of the 1H NMR spectrum it was determined that the copolymer contained 8.9 mole % isosorbide, 2.4 mole % DEG and had an Mn=14,900 g/mole.

It has been successfully demonstrated that isosorbide-5-(4-carbomethoxybenzoate) (1) provides a convenient route for incorporation of isosorbide into PET. The isosorbide/PET copolymer formed showed an increase in Tg of 7.5° C. with an incorporation of 8.9 mole % isosorbide. This is consistent with the expected rise in Tg with addition of isosorbide to PET as reported in the literature. No catalyst was added to the polymerization since it was assumed that sufficient catalyst remained in the starting PET to catalyze the transesterification with 1.

CONCLUSIONS

It has been successfully demonstrated that: (a) A new class of polymers can be made from AB monomers based on isosorbide and its isomers and that these homopolyesters have Tg>150° C. and are semi-crystalline; (b) AB monomers can be used to incorporate isosorbide into PET to raise Tg; and (c) these results provide strong incentive for further studies on the incorporation of AB monomers based on isosorbide and its isomers into a variety of polymers to modify their properties.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. An AB monomer comprising bisanhydrohexitol derivatives capable of self-polymerization directly to form a sterioregular or regioregular condensation polymer, wherein the AB monomer has the structure:

wherein:
a. A is a carboxylic acid, an ester, or an acid chloride,
b. Y is a bisanhydrohexitol unit derived from isosorbide, isoidide or isomannide;
c. X is selected from the group consisting of:
i. aromatic rings, including 1,4-phenylene, 1,3-phenylene, 2,6-naphthalene, 2,7-naphthalene or substituted derivatives thereof;
ii. substituted or unsubstituted heterocycles, and
iii. saturated or unsaturated aliphatic chains;
d. B is —OH; and
e. C is an ester carbonyl link with the carbon attached to X and the oxygen attached to Y, and wherein the AB monomer is at least about 98% pure endo-substituted bisanhydrohexitol derivative or an at least about 98% pure exo-substituted bisanhydrohexitol derivative.

2. The AB monomer of claim 1, wherein A is an acid chloride.

3. The AB monomer of claim 1, wherein X is an aromatic ring selected from the group consisting of: 1,4-phenylene, 1,3-phenylene, 2,6-naphthalene, 2,7-naphthalene and substituted derivatives thereof.

4. The AB monomer of claim 1, wherein X is selected from the group consisting of, 2,5-furan 2,5-thiophene, substituted 2,5-furan and substituted 2,5-thiophene.

* * * * *